United States Patent [19]

Munk

[11] Patent Number: 4,942,018

[45] Date of Patent: Jul. 17, 1990

[54] PACKED BED GRADIENT GENERATOR FOR HIGH PERFORMANCE LIQUID CHROMATOGRAPHY

[75] Inventor: Miner N. Munk, Lake Park, Fla.

[73] Assignee: LDC Analytical Inc., Riviera Beach, Fla.

[21] Appl. No.: 328,750

[22] Filed: Mar. 23, 1989

Related U.S. Application Data

[63] Continuation of Ser. No. 13,124, Feb. 10, 1987, abandoned.

[51] Int. Cl.$^5$ .............................................. G01N 30/02
[52] U.S. Cl. ....................................... 422/70; 422/81; 436/161; 73/61.1 C
[58] Field of Search ...................... 422/68, 70, 81, 100, 422/101; 436/52, 161, 174, 179; 73/61.1 C

[56] References Cited

U.S. PATENT DOCUMENTS 3,934,456  1/1976  Munk .................................... 73/61.1
4,130,394  12/1987  Negersmith ..................... 422/100 X

OTHER PUBLICATIONS

Henley et al; Equilibrium-Stage Separation Operations in Chemical Engineering; John Wiley & Sons, Inc; New York; 1981 pp. 72–73.
L. Synder and J. Kirkland; "Introduction to Modern Liquid Chromatography"; 1979, pp. 663–719, 840–843.
L. Snyder; "Comparisons of Normal Elution, Coupled-Columns, and Solvent, Flow or Temperature Programming in Liquid Chromatography"; Journal of Chromatographic Science; vol. 8; Dec., 1970, pp. 692–706.
P. Jandera and J. Churacek; "Gradient Elution in Column Liquid Chromatography"; 1985, pp. 185–242.
J. Giddens; "Dynamics of Chromatography"; 1965, pp. 86–89.

Primary Examiner—Barry S. Richman
Assistant Examiner—Timothy M. McMahon
Attorney, Agent, or Firm—Woodcock Washburn Kurtz Mackiewicz & Norris

[57] ABSTRACT

Solvent composition gradients in high performance liquid chromatography (HPLC) are generated with a packed bed gradient generator. Natural dispersion occurs in flow through a bed of particles due to eddy and molecular diffusion. This dispersion changes a sharply defined front between two solvents into a desirable error function type gradient profile at the interface between the solvents. The packed-bed gradient generator is a cylindrical tube filled with chemically inert glass beads. Other axial column contours such as a double taper column or bell-shaped entrance and exit regions can be used to tailor the gradient profile. The static packed-bed gradient generator can be placed either on the low pressure inlet side of the high pressure pump, or the high pressure outlet side of the pump. While low pressure operation may provide added convenience, high pressure operation provides additional pulse dampening ability. The high pressure placement of the packed-bed generator would be the only option for use with syringe pumps common in microbore HPLC.

4 Claims, 18 Drawing Sheets

PLATE HEIGHT VERSUS FLOW RATE FOR CHEMINERT GLASS COLUMN WITH 280 mm LONG BY 1/4" DIAMETER BED OF 3mm DIAMETER KIMAX GLASS BEADS

PACKED BED GRADIENT GENERATOR FOR HIGH PERFORMANCE LIQUID CHROMATOGRAPHY

This is a continuation of application Ser. No. 013,124, filed Feb. 10, 1987, now abandoned.

BACKGROUND OF THE INVENTION

Solvent composition gradients are widely used in high performance liquid chromatography to circumvent the so called "general elution problem" encountered in isocratic (constant solvent composition) analysis where early eluting peaks are closely bunched and later peaks are spread progressively further apart in the chromatogram. By an appropriate choice of solvent gradient, it is often possible to retain the necessary resolution for separation of the early peaks while speeding the elution of the later peaks and, therefore, shortening the overall analysis time. The later peaks are also narrower under gradient elution, and diluted in less solvent so that detectability limits for these peaks are improved over isocratic conditions.

Versatile solvent gradient systems are available from several instrument manufacturing companies, but these systems tend to be considerably more expensive than isocratic solvent delivery systems. While these gradient solvent delivery systems offer great versatility, there are probably many applications where versatility could be sacrificed for cost as, for example, in dedicated analyzers, where the gradient profile could be optimized on one of the expensive gradient systems and transferred to a lower cost, less versatile system. For another perspective, gradient capability could be added to isocratic dedicated analyzers for little additional cost.

Gradient systems are usually classified as "low pressure" in which the gradient is formed on the inlet or low pressure side of the pump, or "high pressure" in which the gradient is formed on the outlet or high pressure side of two or more pumps. The low pressure gradient systems only require one high pressure pump, and are, therefore, usually less expensive than high pressure gradient systems. There are special problems that must be overcome in the design of a low pressure gradient system. The mechanically reciprocating, check valve type pumps commonly used in HPLC, draw solvent into the cylinder in discrete steps and tend to create a stair-step type gradient profile unless a detrimental mixing volume is placed downstream of the pump to smooth out these steps.

A more difficult problem can arise when switching valves are used to generate the gradient profile. If these valves do not operate at a high frequency compared to the pump frequency, or are not purposely synchronized with the pump frequency, random variation between the switching valve and the pump phases can generate significant departures from the intended gradient profile. The high pressure gradient systems place stringent requirements on the flow rate repeatability of the high pressure pumps near the end points of the gradient. Of particular importance is the flow rate repeatability at the lowest flow rate where mechanical, reciprocating check valve pumps tend to have problems because of check valve and main seal leakage. These problems have been solved to a satisfactory level for standard bore HPLC, where flow rates are apt to lie between $\frac{1}{2}$ and 5 milliliters per minute, but their solution has added to the cost of the gradient solvent delivery systems.

While mechanically reciprocating check valve pumps dominate in standard bore HPLC, the low flow rates of microbore HPLC (typically between 1 and 100 microliters per minute) strain the present state of check valve technology, and, as a result, single stroke syringe pumps that do not require check valves are most common. Low pressure gradient formation is not practical with these pumps because of their large hold-up volume. The high gradient formation by mixing flow from two or more syringe pumps can be a problem with some commonly used gradients such as methanol/water and acetonitrile/water because of a peculiar oscillating mode that develops from differences in viscosity and compressibility of the two solvents and their mixtures. This oscillating mode can be eliminated by the use of a constant back pressure valve downstream of the point of solvent mixing and ahead of the column, or the use of individual back pressure regulating valves at the output of each pump.

While not used in commercial HPLC gradient solvent delivery systems of current vintage, various mixing chamber type gradient generators have been reported in the literature. These devices use a stirred mixing chamber of fixed or variable volume that is initially filled with the first solvent of the gradient. The second end point solvent of the gradient is pumped into this mixing chamber to change its composition with time, and, thus, generate the solvent gradient. The simplest of these is the exponential dilution chamber which has a fixed volume. Unfortunately, the exponential dilution chamber generates a convex upward gradient profile that is generally undesirable in HPLC. This type of profile is steepest at the beginning of this separation where the peaks are already more tightly bunched in time, and levels out in the last part of the separation where it is usually desirable to bring widely spaced peaks closer together.

More desirable profiles are obtained theoretically by connecting a number of exponential dilution chambers in series. Equations for the gradient profiles of one, two, three, and four exponential dilution chambers connected in series are commonly known to those skilled in the art. These equations have been used to calculate the curves plotted in Graph I. As the numbers of chambers increases, the initial steepness of the curves become less and the curves approach the shape of the error function plotted in Graph II. It will be clearly understood by those skilled in the art that the error function is the shape of the concentration profile in frontal chromatographic analyses where the sample is introduced at the head of the column as a steep function.

It would be desirable to generate the desirable error function type gradient, approximated with a large number of exponential dilution chamber in series, by a packed bed. A packed bed would be much less expensive than a series of exponential dilution chambers and much more reliable.

A packed-bed gradient could consist of some sort of column filled with suitable packing material such as millimeter size chemically inert glass beads. The relatively large beads would offer little flow resistance and the pressure drop across the bed would be low for the flow rates used in HPLC. The millimeter sized beads would be of the order of 1000 times larger than the micrometer sized particles used in efficient HPLC columns. Pressure drop varies proportionally to the inverse square of the particle diameter. Thus, the pressure drop across a packed-bed gradient generating column would be of the order of one million times less than that across a chromatographic column if they are of comparable length and diameter.

Because of its inherent low pressure drop the packed-bed gradient generating column could be placed on the low pressure, inlet side of the pump, as well as on the high pressure, outlet side of the pump. Low pressure operation of the packed bed would allow use of less expensive low pressure fittings and valves, and use of a low pressure column. A transparent glass column might be used for visibility of the bed. On the other hand, high pressure operation would provide a built in pulse dampener, due to compressibility of the solvent in the bed, to dampen the pulses from lower cost pulsating pumps. The pulse dampening feature could be enhanced by the use of a flexible wall column such as a bourdon tube. The high pressure gradient capability of the packed bed generator makes it compatible with high pressure syringe pumps used in microbore HPLC.

SUMMARY OF THE INVENTION

In accordance with the present invention a system for the generation of solvent composition gradients utilizes a packed bed gradient generator. The invention utilizes two pumping means to pump respective first and second chemical solvents through a packed bed gradient generator on to a chromatographic column and detector. The packed bed gradient generator consists of a cylindrical tube having both inlet and outlet ports. Attached to each port is a valve fitting which allows the inflow and outflow of solvent. Within the column are two adjustable sliding end seals which when separated, create an internal gradient bed. The gradient bed is packed with chemically inert spherical glass beads, which can act to dampen the pulsations on the high pressure side, to create a gradient profile.

DESCRIPTION OF THE PREFERRED EMBODIMENT

The device for the generation of solvent composition gradients of the preferred embodiments is shown with reference to the disclosed figures in which the same numbers are used.

Figures 1, 4:
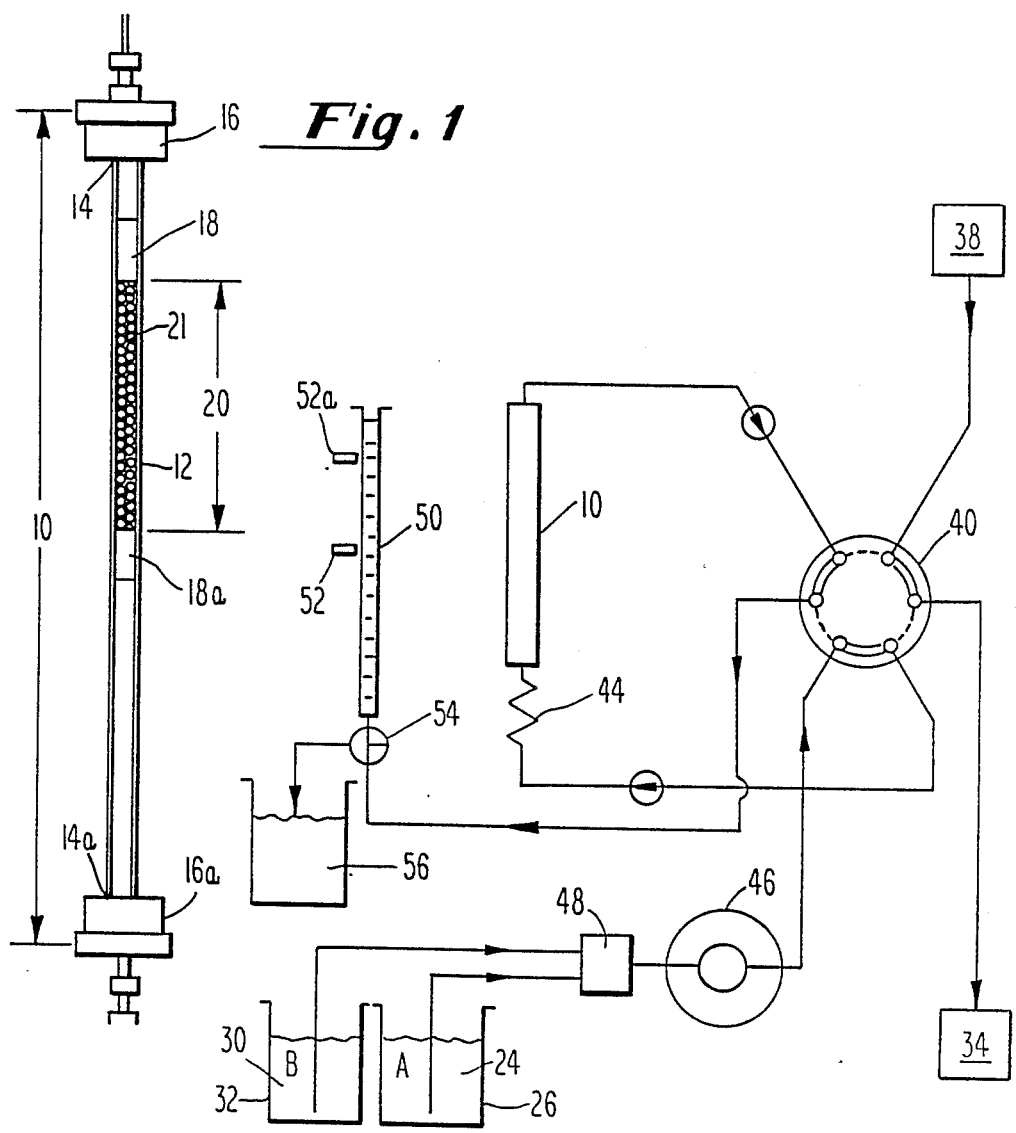
FIG. 1 is a side view of the packed bed gradient generator of the preferred embodiment.
FIG. 4 is a diagram of a modification of the system shown in FIG. 3 in which the entire solvent loading procedure is accomplished automatically;.

Referring to FIG. 1, the packed bed gradient generator 10 of the preferred embodiments is illustrated. It consists of a hollow cylindrical tube 12 having interior sidewalls, an inlet port 14 and an outlet port 14a. Attached to inlet and outlet ports 14, 14a are respective inlet and outlet fittings 16, 16a. Inlet and outlet fittings 16, 16a each have an orifice for permitting the flow of solvent into and out of hollow cylindrical tube 12. Within hollow cylindrical tube 12 are sliding end seals 18, 18a which when separated, create a gradient bed 20 within the interior walls of the tube. Internal volume 20 is then filled with a suitable packing material such as millimeter sized spherical glass beads 21. Chemically resistant borosilicate beads with diameters of of 3, 4, 5, and 6 millimeters (mm) are readily available from laboratory supply companies at moderate cost and are suitable as the packing material 21. Depending upon column geometry, both 3 mm and 4 mm chemically inert spherical glass beads 21 can be used to pack the gradient bed 20. Thus, experimentally, 3 mm glass beads were utilized in cylindrical columns having an internal diameter of ¼" and ½", and 4 mm were utilized in the 1" diameter cylindrical columns.

Suitable materials for the body of the hollow cylindrical tube 12 are chemically inert glass tubes having inside diameters of ¼", ½" and 1" respectively, a 10 ml calibrated pipet barrel, a double-taper stainless steel column and an 8 mm inside diameter by 480 mm long stainless steel column. Sliding end seals 18, 18a permit variation in the length of the gradient bed 20. The hollow cylindrical tube has end grooves for holding the sliding end seals 18, 18a. A 280 millimeter gradient bed was used experimentally for the ¼" and ½" diameter hollow columns, and a gradient bed length of 100 mm was used for the 1" diameter column, but the best dimensions will depend on the particular application.

FIG. 1 illustrates a hollow cylindrical tube 12 composed of a chemically inert transparent glass, which allows visual observation of the bed packing structure and colored dye patterns. It is noted that this material is limited to low pressure applications. Hollow cylindrical tube 12, when composed of a material such as stainless steel with sufficient thickness would be able to withstand internal pressures in excess of 15,000 psi.

Spherical packing beads 21 offer little flow resistance as a packing material, and the pressure drop across gradient bed 20 is low for the flow rates used in HPLC. It will be understood by those skilled in the art that the millimeter sized beads 22 are on the order of 1000 times larger than the micrometer sized particles used in efficient HPLC detection columns. Because pressure drop is approximately equal to the inverse square of particle diameter, the pressure drop across the packed bed gradient column 10 will be approximately one million times less than across a chromatographic column of comparable length and diameter.

Because of its inherent low pressure drop, the packed bed gradient generating column 10 could be placed on the low pressure, inlet side of the pump, as well as on the high pressure, outlet side of the pump. Low pressure operation of the packed bed would allow use of less expensive low pressure fittings 16, 16a, and use of a low pressure tube. A transparent glass tube might be used for visibility of the gradient bed 20. On the other hand, high pressure operation would provide a built-in pulse dampener, due to compressibility of the solvent in the bed, to dampen the pulses from lower cost pulsating pumps. The pulse dampening feature could be enhanced by use of a flexible wall column, such as a bourdon tube. The high pressure gradient capability of the packed bed generator makes it compatible with the high pressure syringe pumps used in microbore HPLC.

Two alternative embodiments of a system using of the packed bed gradient generator 10 of the preferred embodiment are shown. Both systems disclosed are for placement of the packed gradient generator 10 after a high pressure pump, because the pulse dampening feature allows for use of a low cost pulsating pump for dedicated analyzers where cost is a primary consideration, and high pressure placement of the packed bed gradient generator is the only one compatible with the syringe pumps used on microbore HPLC. However, it will be obvious to those skilled in the art that both embodiments shown can be extended to low pressure operation of the packed bed generator 10.

Figure 2:
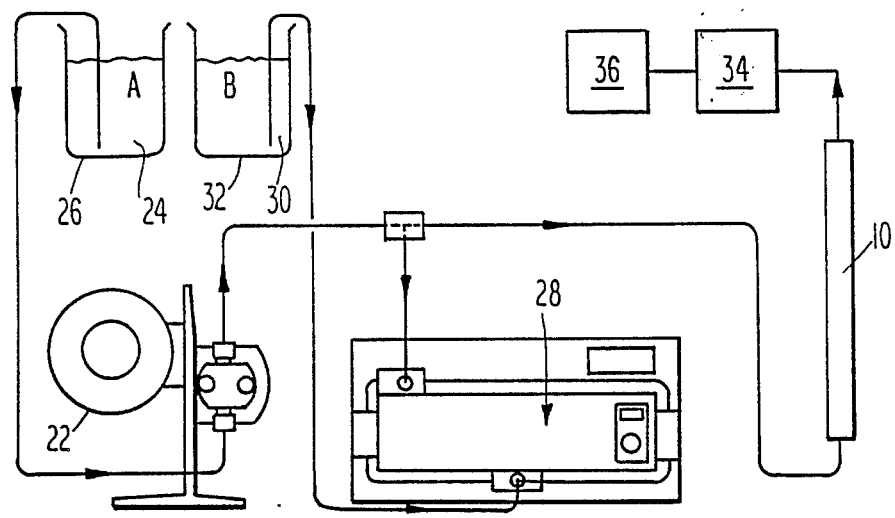
FIG. 2 is a diagram of a complete system utilizing the packed bed gradient generator in which there is independent equilibration of the system with a first solvent before the start of the pumping of the second solvent.

Referring to FIG. 2, the first system embodiment utilizing the packed bed gradient generator 10 is shown. This embodiment was utilized to used to obtain a first set of experimental gradient profiles. This system was designed to generate a two-solvent gradient, and comprises a first metering pump 22 used to pump a first solvent 24 (solvent A) from a first storage reservoir 26 (reservoir A) and a second metering pump 28 used to pump a second solvent (solvent B) 30 from a second storage reservoir 32 (reservoir B) through packed bed gradient generator 10 into the sample injector 33 chromotographic column 34 and detector 36. Both metering pumps 22 and 28 may be of conventional design and numerous such pumps are readily available on the market. For example, an LDC-Milton Roy Simplex Mini-Pump Metering Pump can be used as metering pump 22 to pump solvent A 24 from reservoir A 26 and an LDC Milton Roy Constomeric III Metering Pump can be utilized to pump solvent B 30 from reservoir B 32. Detector 36 may be any commericially available chromatographic detector such as the Spectromonitor D detector.

Referring to FIG. 2, metering pump 22 is initially used to pump solvent A 24 from reservoir A 26 through the packed bed gradient generator 10, injector, chromatographic column 34, and detector 36, which purges the system with solvent A prior to the chromatographic run. After purging the system with solvent A 24, metering pump 22 is turned off, and metering pump 28 is turned on to start flow of solvent B 30 through packed bed gradient generator 10.

The interface between solvent A and solvent B develops into an error function profile in the packed gradient bed 20 as flow continues. This error function solvent composition profile is directed to the sample injector 33, chromatographic column 34, and detector 36. This arrangement requires that metering pump 22 be capable of pressure delivery sufficient to generate flow rates across chromatographic column 34 comparable to those generated by metering pump 28, so that chromatograph 34 column can be equilibrated with solvent A in a reasonable length of time. While metering pump 22 must be a high pressure pump in this arrangement, it does not have to be an expensive pulseless pump, because it is not in operation during the separation, and its pulses do not interfere with sample detection. Packed gradient bed 20 should sufficiently dampen the pulses from metering pump 22 during equilibration with solvent A so that they do not damage chromatographic column 34. The Milton Roy LDC Mini-Pump with its reputation for reliability seems to be a logical choice for this application. Depending upon the pulse dampening ability of packed gradient bed 20 and the level of detection required, metering pump 28 could be a high pressure pulseless pump like the Constomeric III metering pump or a lower cost high pressure pulsating pump. While metering pump 22 only has to have external on-off control with its flow rate set manually for optimum equilibration time of the column, metering pump 28 should have external control of flow rate, as well, for increased versatility.

The arrangement in FIG. 2 provides complete filling of the packed bed with solvent A before the gradient generation is started. The metering of solvent A is done automatically in packed gradient bed 20 and downstream plumbing. Repeatability of the gradient profiles is excellent with this arrangement, but lacks versatility. Only one gradient profile can be generated with each packed gradient bed 20, thus an assortment of packed beds would be required for a range of gradient profiles.

Figure 3:
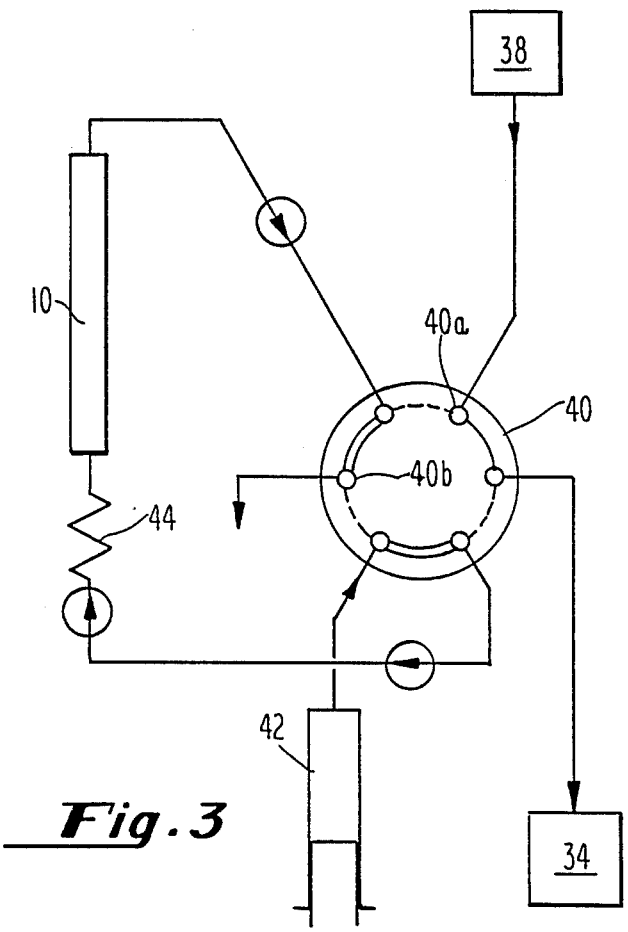
FIG. 3 is a diagram of a system for running multiple gradient profiles with one packed bed gradient generator and a single pump;.
Figure 5:
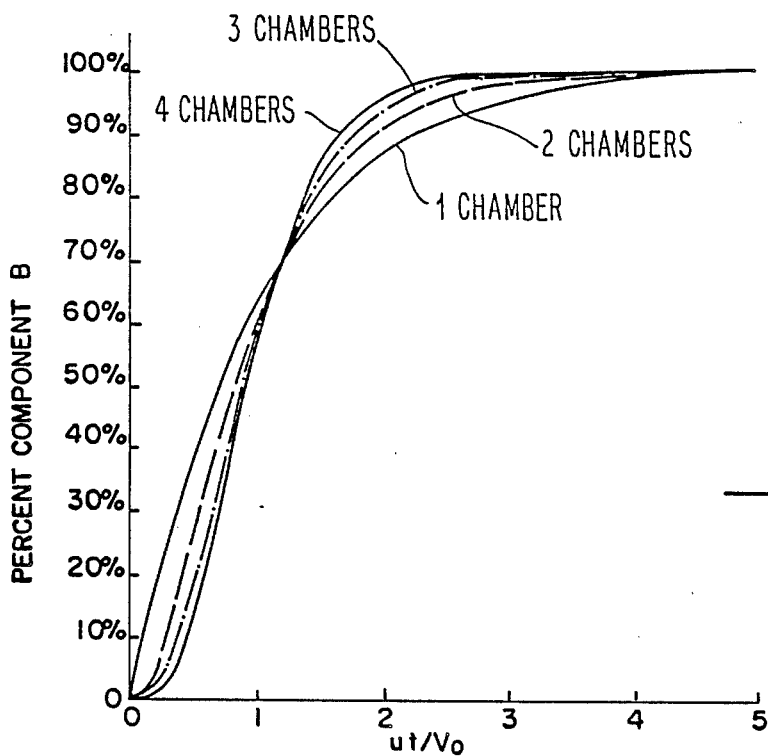
FIG. 5 shows the theoretical gradient profiles produced by one, two, and four exponential dilution chamber, respectively, placed in series;.
Figure 6:
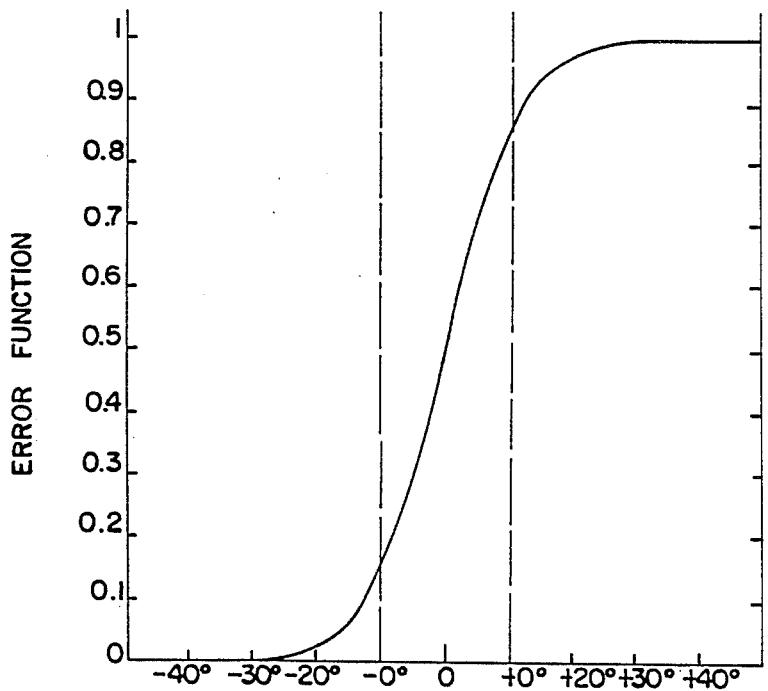
FIG. 6 shows the theoretical error function.
Figure 7:
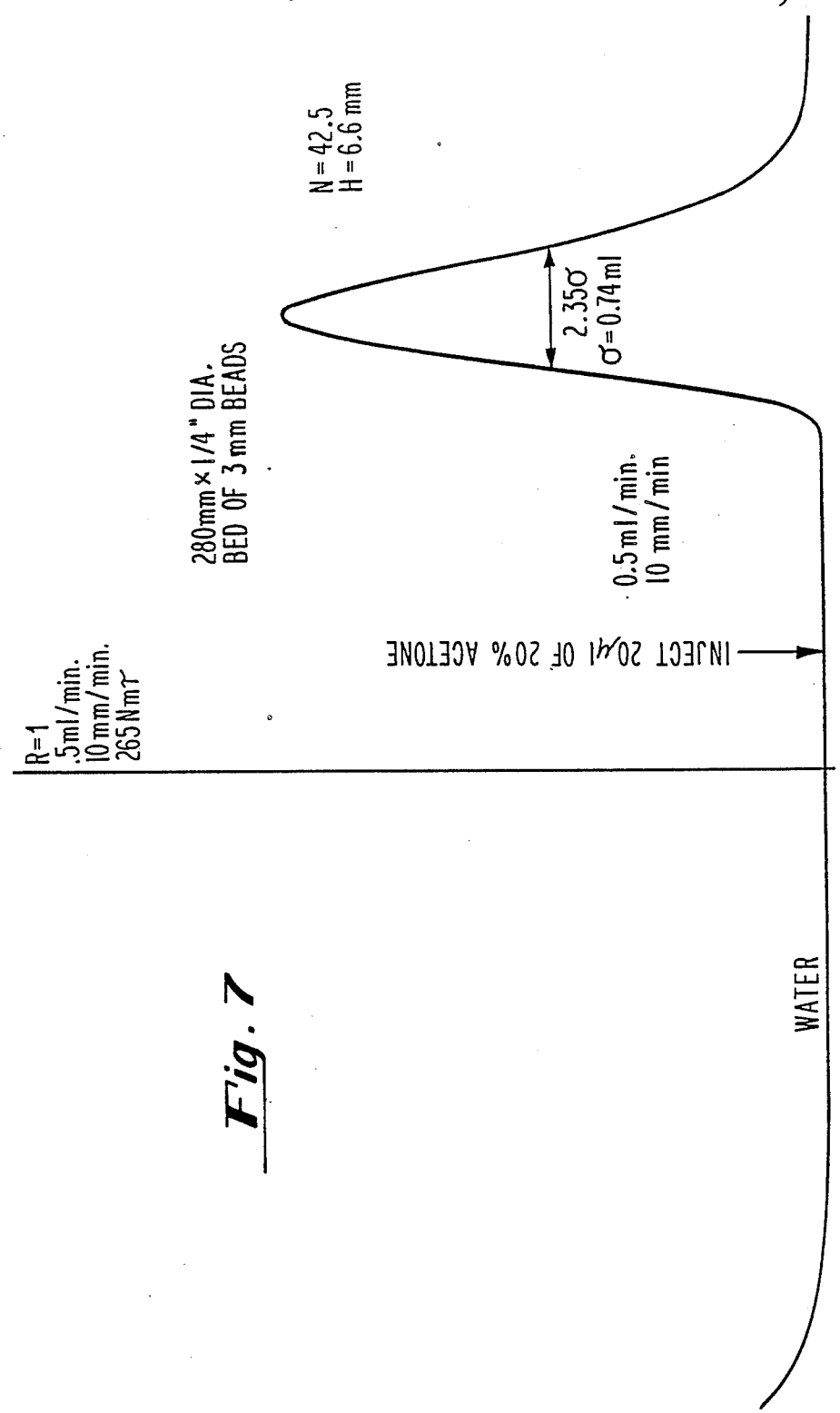
FIGS. 7-18 show peak widths and gradient profiles for different examples.
Figure 8:
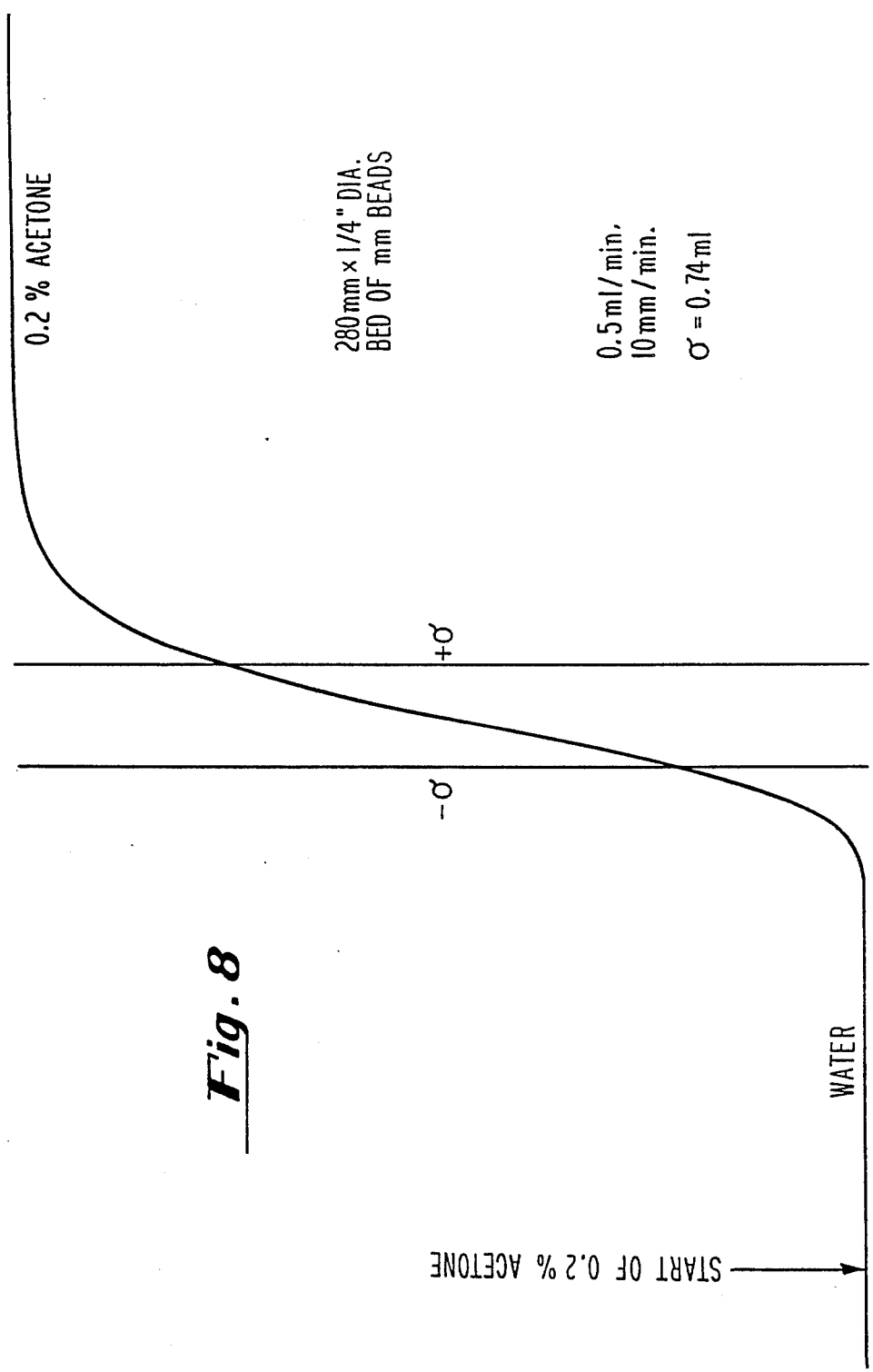
Figure 9:
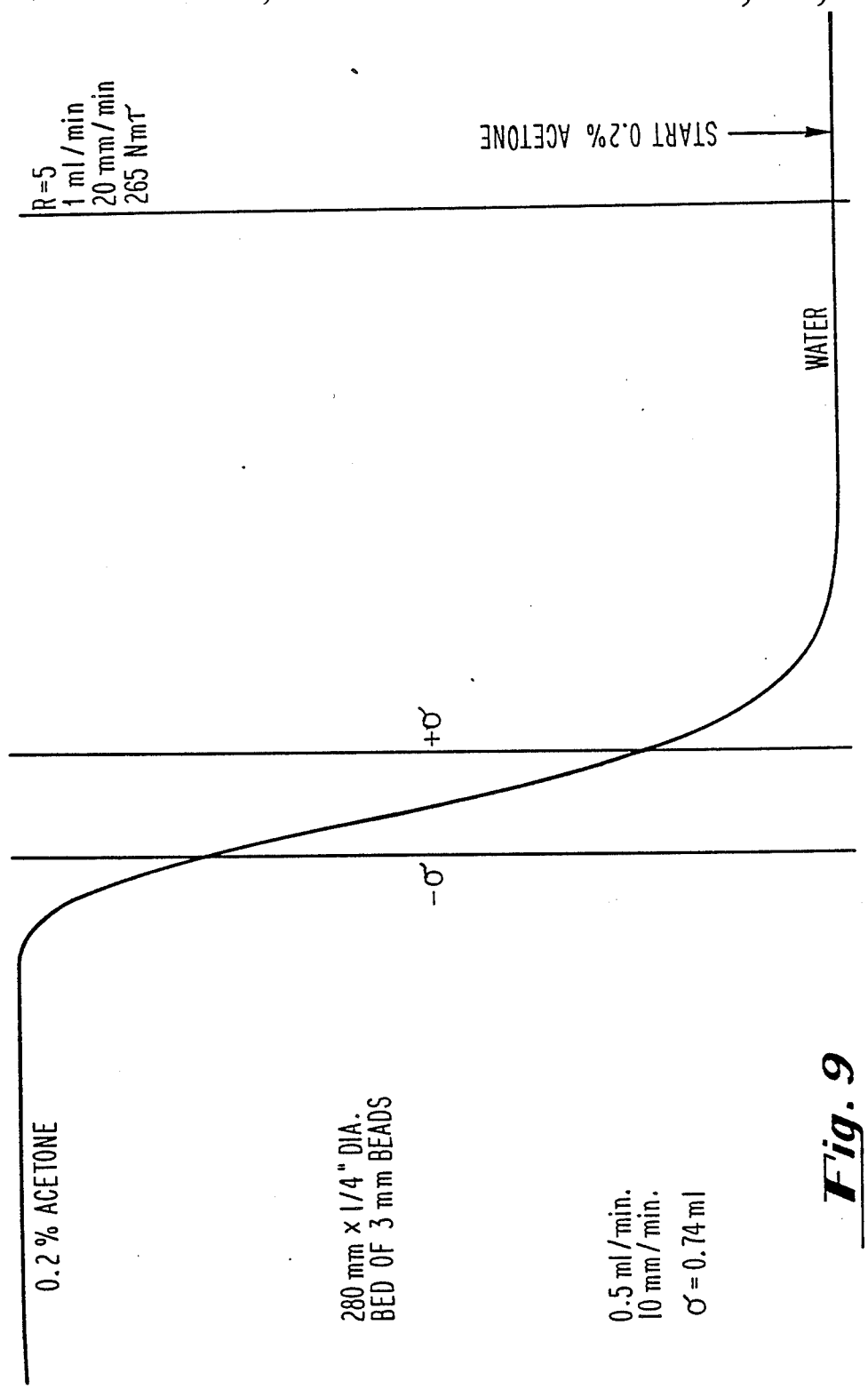
Figure 10:
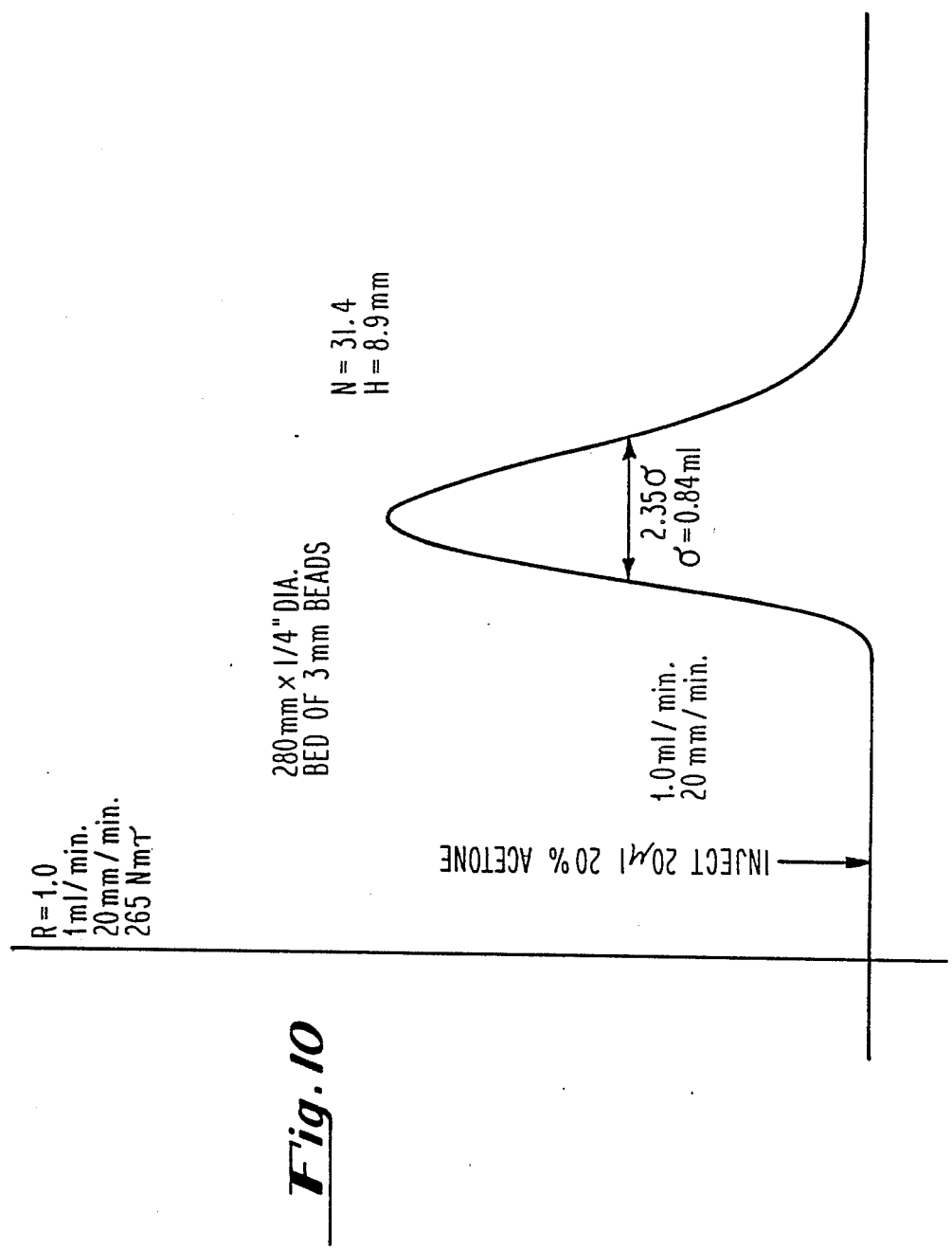
Figure 11:
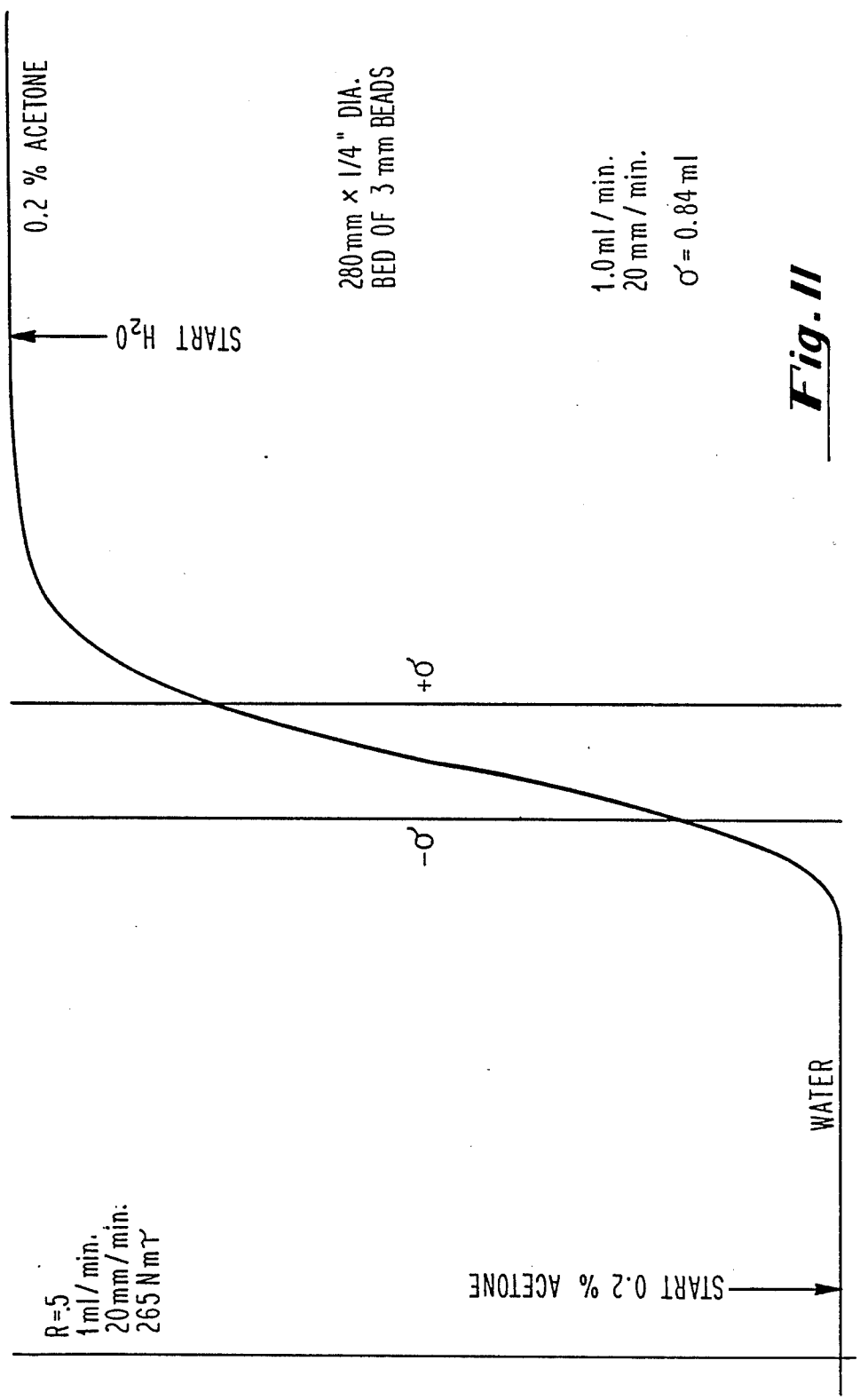
Figure 12:
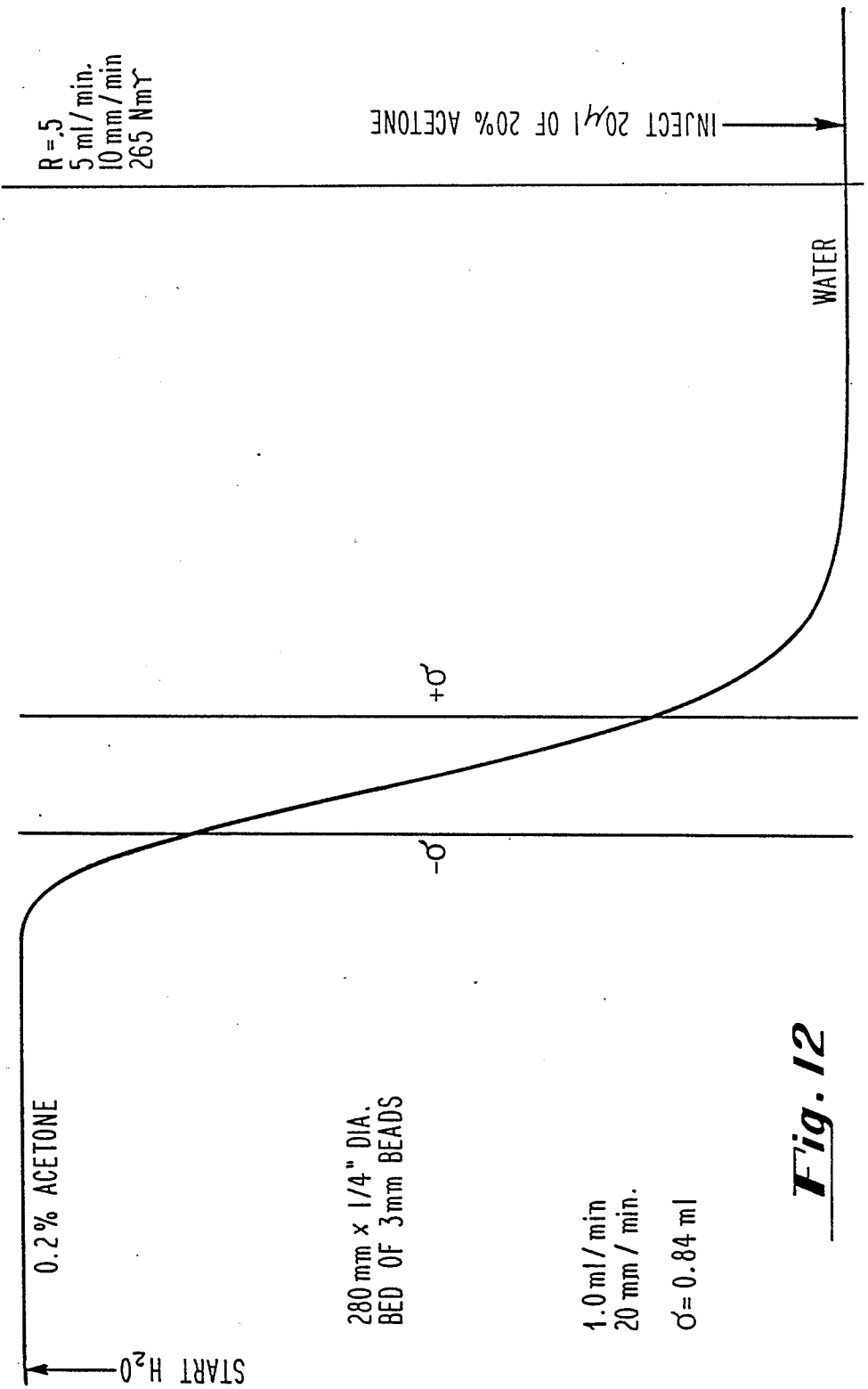
Figure 13:
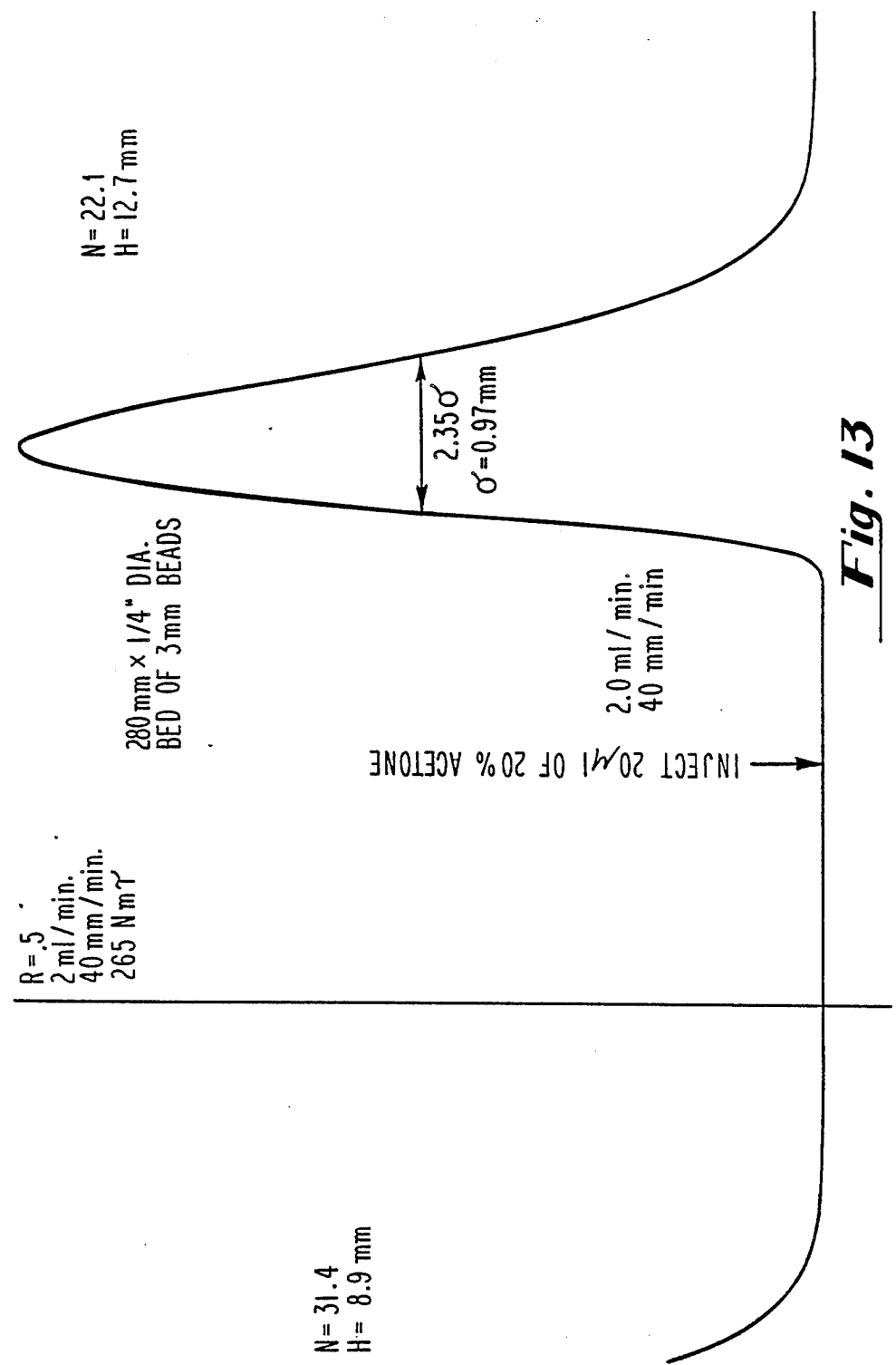
Figure 14:
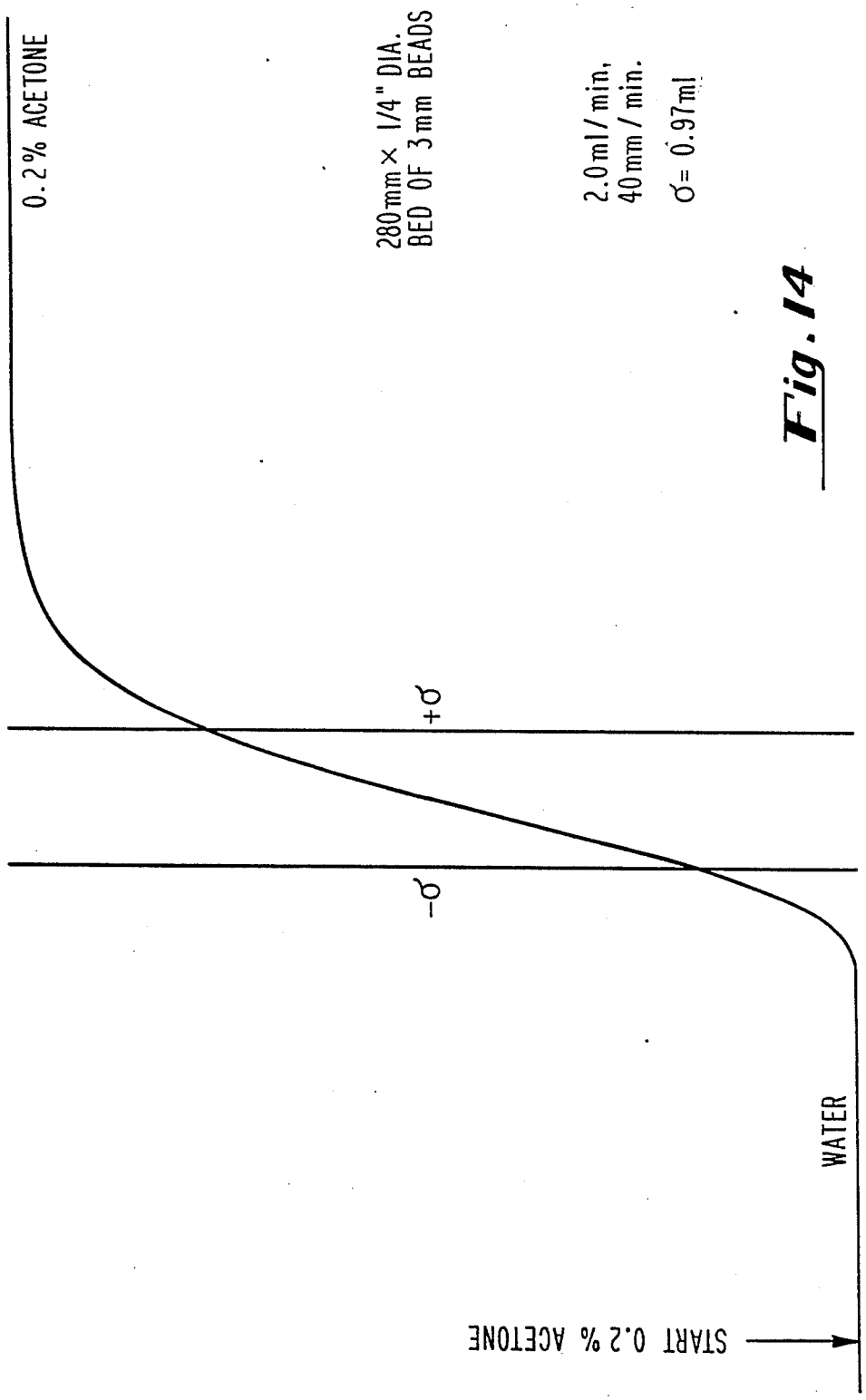
Figure 15:
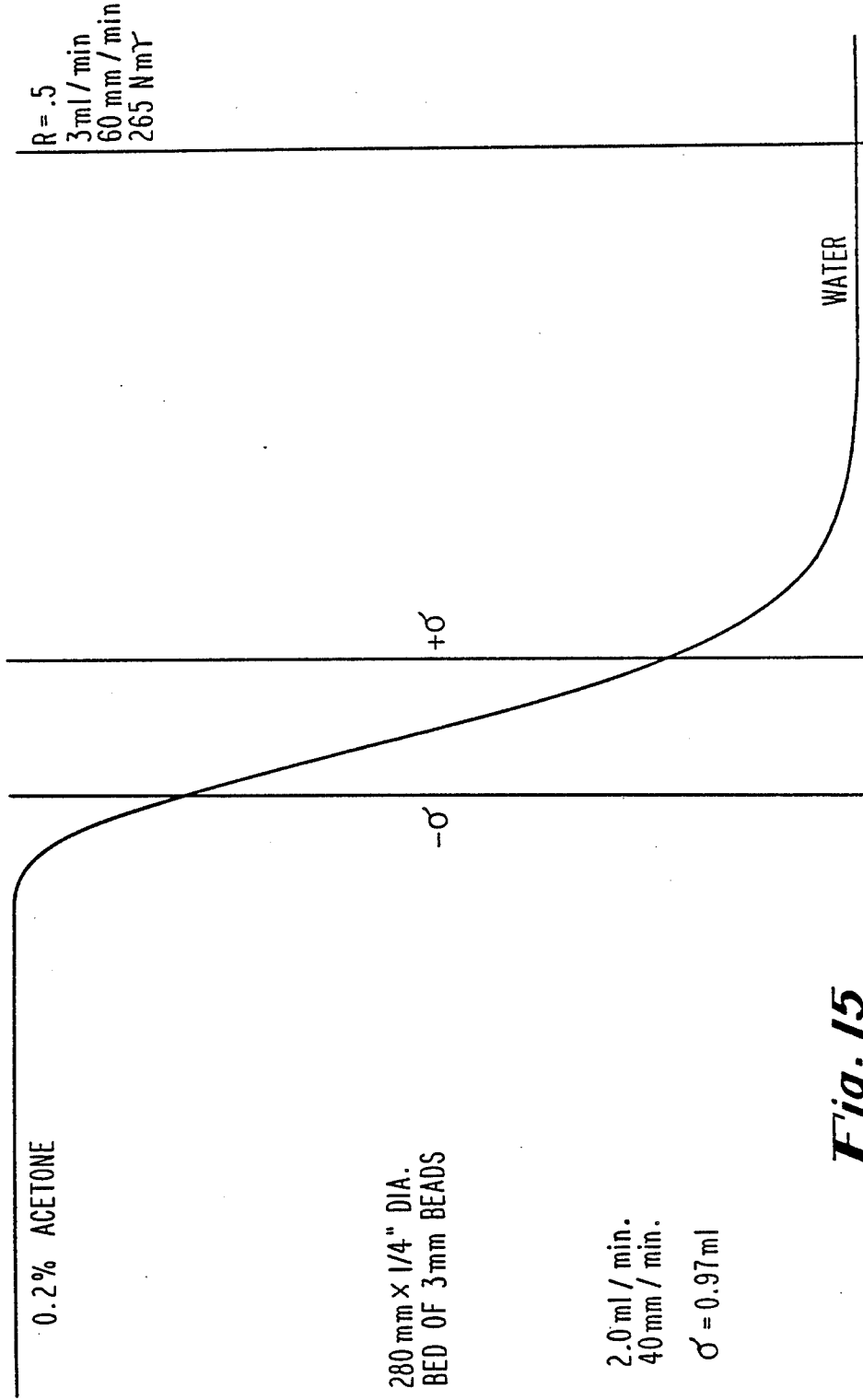
Figure 16:
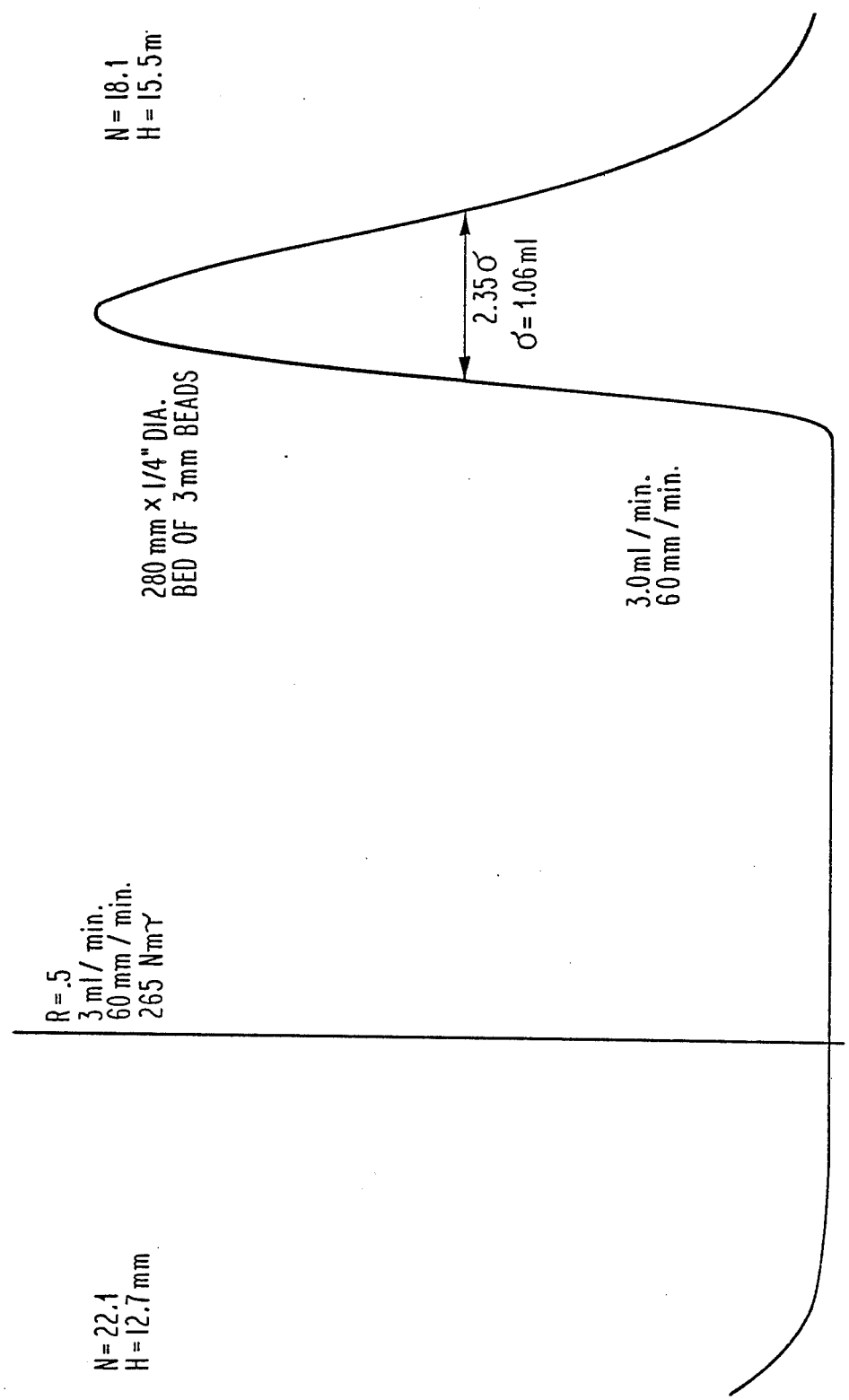
Figure 17:
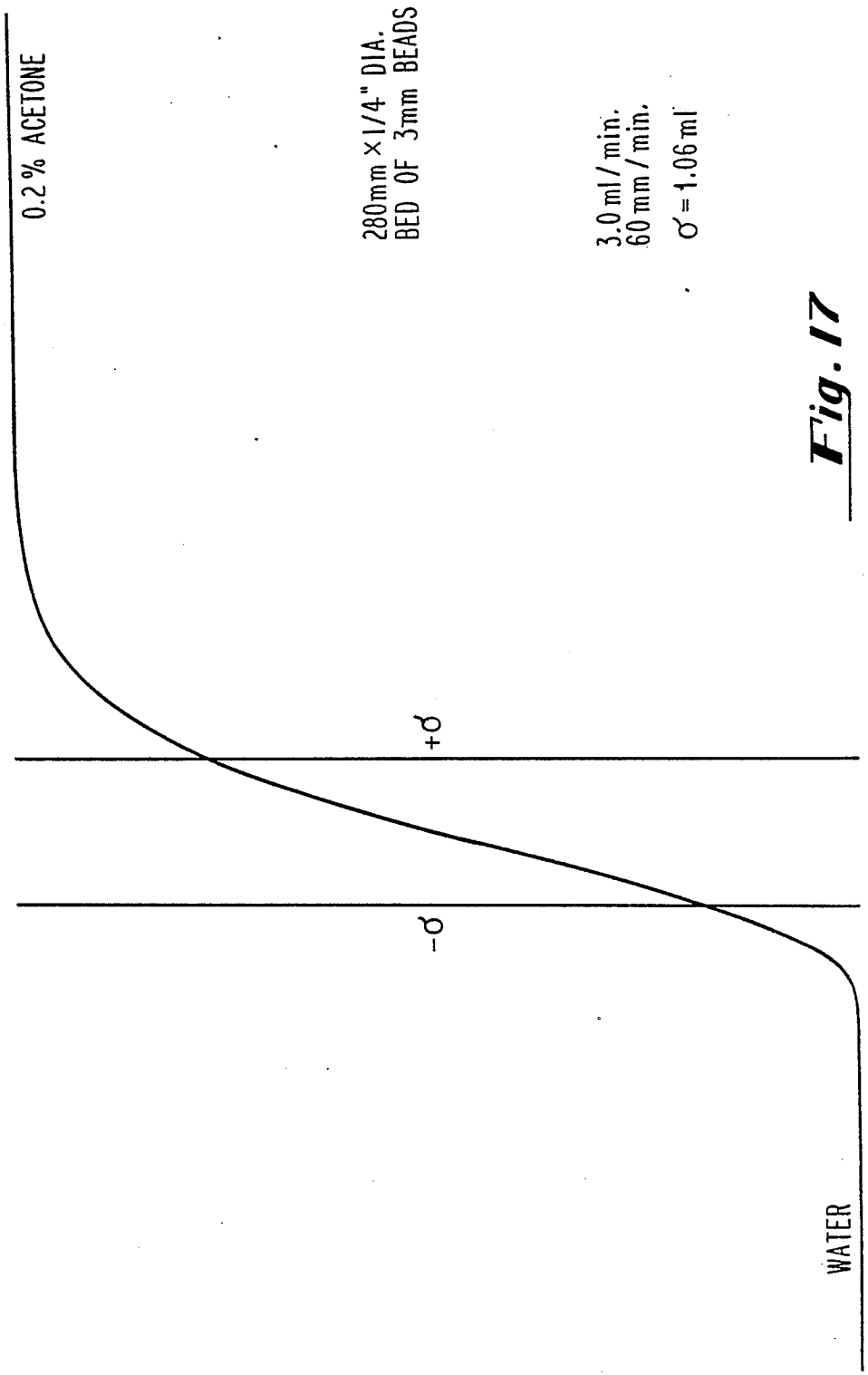
Figure 18:
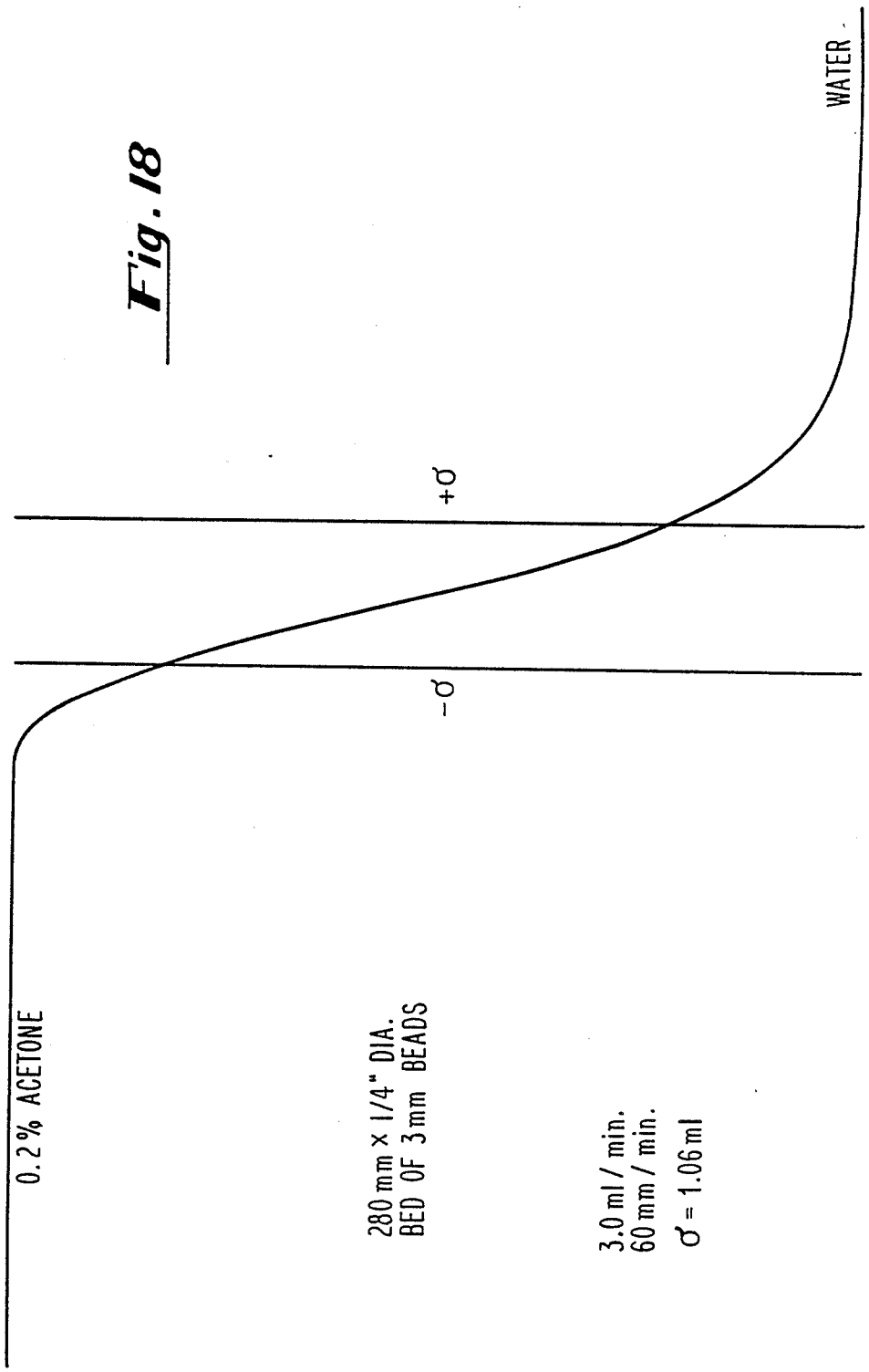
Figure 19:
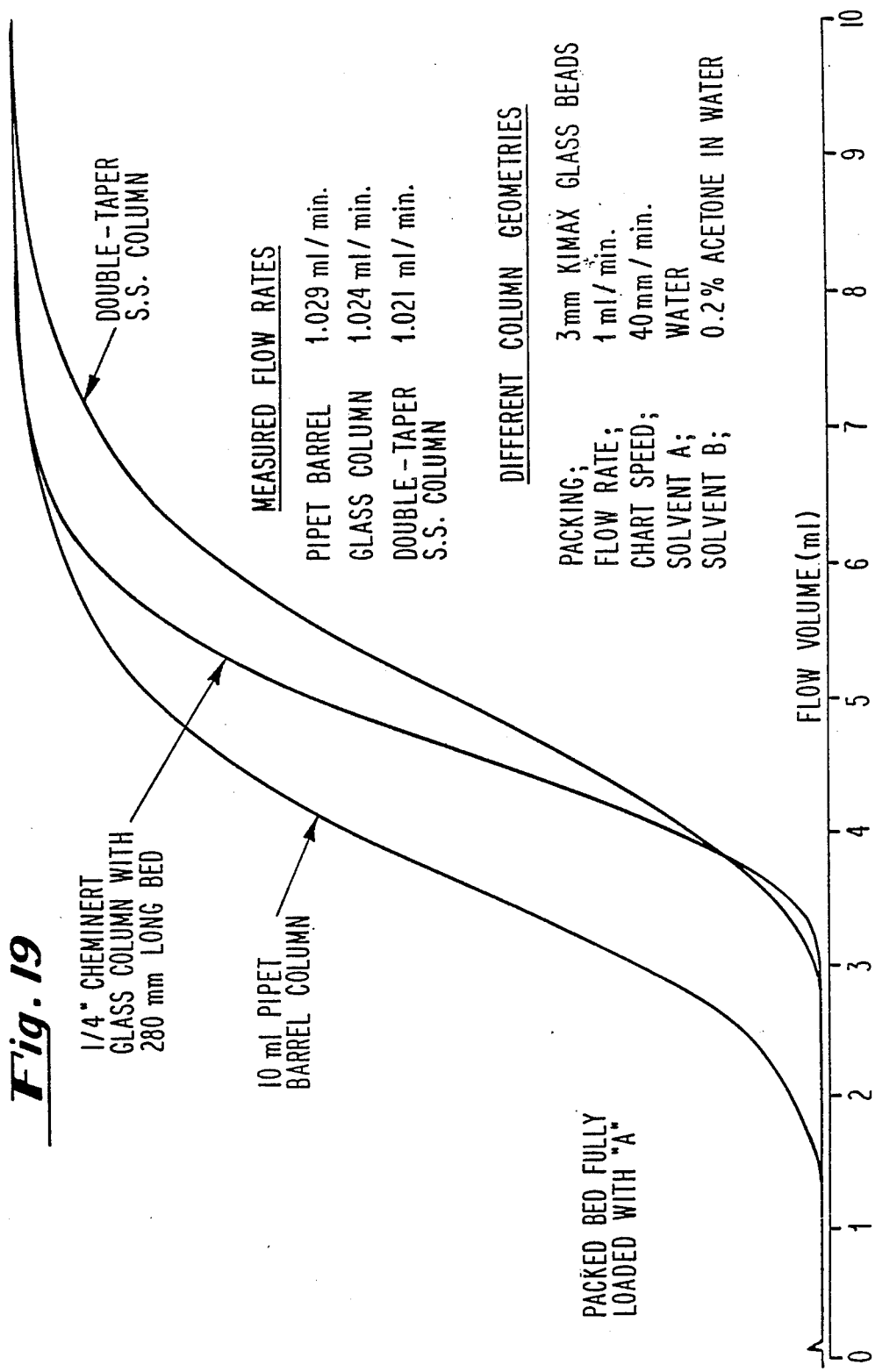
FIG. 19 and 20 show gradient profiles for different column geometries.
Figure 20:
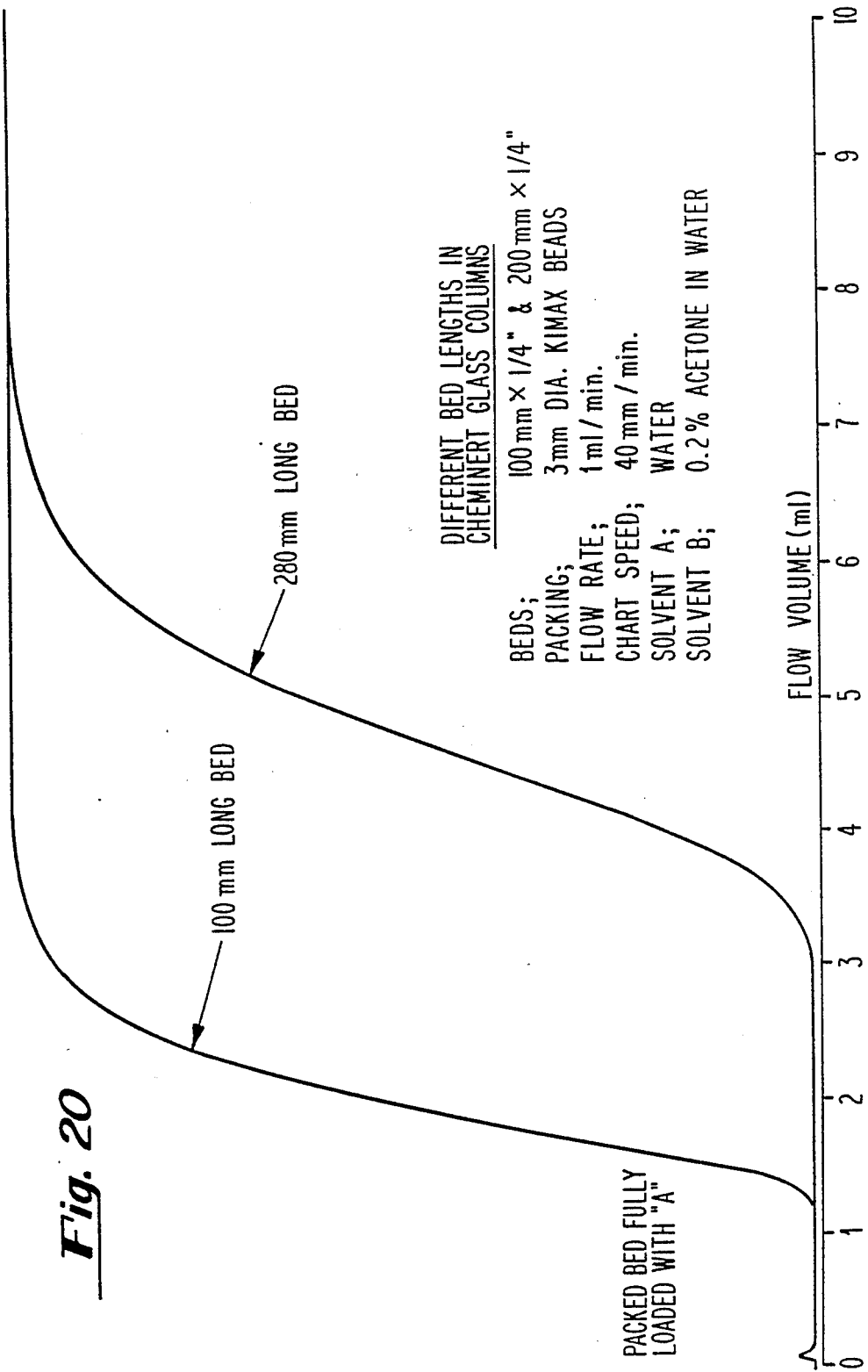
Figure 21:
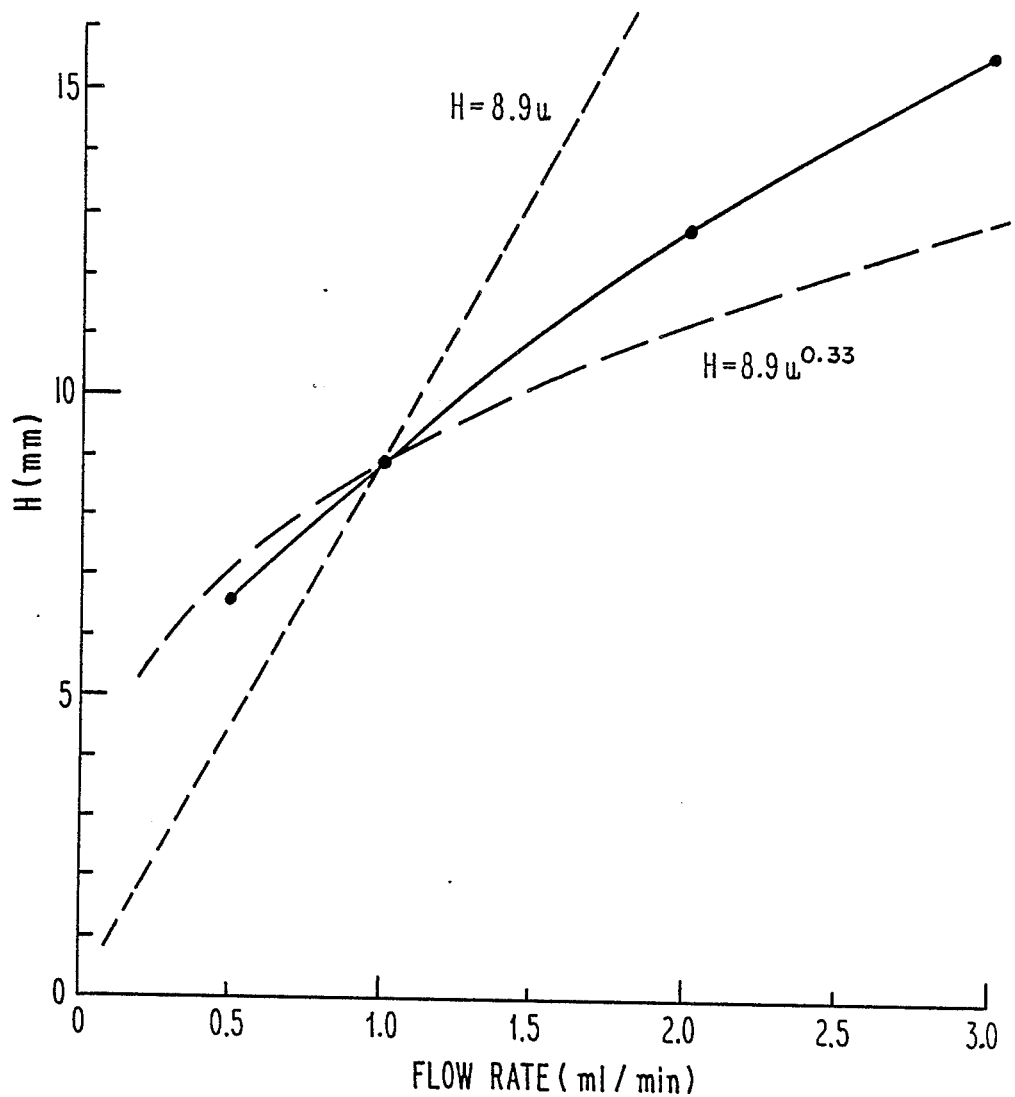
FIG. 21 shows plate height v. flow rate for an exemplary column.

A second convenient and more versatile embodiment utilizing the packed bed gradient generator 10 is illustrated in FIG. 3. This embodiment only requires a single high pressure pump 38. High pressure pump 38 is used to pump solvent B. Packed gradient generator 10 is connected to a six port sample injection valve 40 as a large sample loop would be. The six port injection valve should have both fill port 40a and drain port 40b. An example of such a valve commonly known to those skilled in the art would be the Rheodyne 7010 injection valve With the six port injection valve 40 in the "load" position, the packed gradient bed 20 can be filled with a graduated syringe 42. Such a graduated syringe that is on the market and commonly known to those skilled in the art is the 10 ml Hamilton Gas Tight Syringe.

In this arrangement, the packed gradient bed 20 can be partially loaded with solvent A 24 so that a complete family of gradient profiles can be generated with a single packed gradient bed 20. Solvent A 24 can be metered into the bed by the graduated syringe 42. It will be understood by those skilled in the art that in the alternative, the effluent from the drain port 40b of six-port injection valve 40 can be collected in a graduated cylinder for metering of solvent A 24. Because the system is closed except for the fill and drain ports 40a, 40b of the six port injection valve 40, the amount of solvent A 24 introduced will displace an equal amount of solvent B 30 from the drain port 40b (assuming there is no change in volume upon mixing the two solvents). A series holding coil 44 provides a repeatable volume of solvent A for equilibration of chromatographic column 34 with solvent A when the valve is switched to the "inject" position. Series holding coil 44 in one preferred embodiment consists of a 1.016 mm i.d. by 244.7 cm long coil for applications requiring holding capacities of two milliliters of volume and two such coils in series for applications requiring 4 milliliter volumes. In this system, sample injection from series holding coil 44 is delayed so that chromatographic column 34 is equilibrated with solvent A 24 before the injection.

Referring to FIG. 4, the system could be automated by the addition of a low pressure pump 46, an electrically actuated switching valve 48, and a sight tube 50 with adjustable upper and lower level sensors 52, 52a. In this embodiment, packed gradient bed 20 is capable of generating ternary, quartenary and higher order gradients by successive loading of the different solvent components on the bed. In FIG. 4, packed gradient bed 20 is initially filled with a third solvent, solvent C. Low pressure solvent pump 46 then delivers solvent B 30 from reservoir B 32 until the level in sight tube 50 trips lower level sensor 52. At that time, the electronically actuated switching valve 48 is activated to connect solvent reservoir A to low pressure solvent pump 46, which then pumps solvent A 24 until the level in sight tube 50 activates the upper level sensor 52a and shuts off low pressure solvent pump 46. Level sensors 52, 52a can be mounted so they slide up and down along sight tube 50 thereby adjusting the amounts of solvent B 30 and solvent A 24 delivered to packed gradient bed 20. After the solvents have been delivered to packed gradient bed 20, drain valve 54 at the bottom of sight tube 50 is open to empty it into drain reservoir 56 in preparation for the next run.

While the packed bed gradient generator and three solvent systems for its use are disclosed, it will be understood by those skilled in the art that other embodiments fulfill both the spirit and scope of the claims contained herein.

EXAMPLES

The above discussed embodiments were tested and several different column geometries were experimentally investigated. These included columns composed of LDC Cheminert glass LC columns with inside diameters of ¼", ½", and 1", a 10 mm calibrated pipet barrel, a double-taper stainless column, and an 8 mm inside diameter by 480 mm long stainless steel column. Moreover both 3 mm diameter and 4 mm diameter Kimax brand glass beads were used to pack the gradient beds 20 (FIG. 2).

While not practical for high pressures, the transparent Cheminert columns allowed visual observation of the bed packing structure and colored dye flow patterns. In addition, these columns were equipped with sliding end seals so that the length of the bed could be changed. Bed lengths of 100 mm and 280 mm were used for the ¼" and ½" diameter columns, and a bed length of 100 mm was used for the 1" diameter column. The end tabulations were cut off a 10 ml capacity calibration pipet and the remaining barrel was mounted in a special frame with provisions for connecting 1/16" o.d. stainless steel tubes to the barrel. Two stainless steel columns suitable for high pressures were investigated. The double-taper column tapered from ⅛" at one end to ½" at the center to ⅛" at the other end, and had an empty volume of about 10 ml. The void volume of this double-taper column was measured at 5.21 ml when packed with 3 mm diameter beads. The second stainless steel column had an inside diameter of 8.4 mm and a bed length of 480 mm.

Several experiments were performed utilizing each of the particular column geometries by completely filling the packed gradient bed and downstream plumbing with solvent A before starting the solvent B pump. Most of the experiments were done using a Rheodyne model 7010 six-port injection valve as illustrated in FIG. 3. In these trials, the experiments started with solvent B downstream of the Rheodyne valve so that the traces go from near full chart to near zero to near full chart during the runs. The traces were obtained with a spectromonitor D detector set at 265 nm (absorption maximum of acetone). Overlapping traces were obtained by lifting the recorder pen and rewinding the chart to a common starting point. The large volume loads of solvent A were metered with a graduated cylinder at the drain outlet of the valve, and the smaller load volumes were metered by a 10 ml gas tight syringe and checked by a graduated cylinder at the drain outlet. In the cases of the methanol/water gradients, all metering of solvent A was done with a graduated cylinder at the drain outlet.

The solvent B was pumped with a Milton Roy/LDC ⅓ speed Constametric III pump. The flow rate of this pump was checked periodically by timing flow into a graduated cylinder. The solvent B was doped with 0.2% acetone to give an offset proportional to % B in the traces from the spectromonitor D detector.

The initial set of experiments were performed with a Cheminert ¼" diameter transparent column similar to that shown in FIG. 1. The column was packed with 3 mm diameter Kimax glass beads, as shown to a bed length of 280 mm. The ¼" bore (6.35 mm) was slightly larger than two measured bead diameters (3.10 +0.03 mm), and the beads were observed through the transparent column wall to pack neatly in diagonal pairs with successive pairs rotated 90° with respect to each other. Graphs 1–12 show peak widths and gradient profiles obtained with this column at flow rates of 0.5, 1.0, 2.0, and 3.0 ml/minute. The peaks in Graphs 1, 4, 7, and 10 were obtained by injecting 20 microliters of 20% acetone just ahead of the packed gradient bed. These peaks allowed the calculation of plate numbers and plate heights in accordance with the usual procedures of liquid chromatography. The following mathematical formula will be readily understood by those skilled in the art:

Plate Number, $N = 5.54 (V_r/W_{\frac{1}{2}})^2$

Standard Deviation, $0.425 W_{\frac{1}{2}}$ where $V_r$ is the measured retention volume and $W_{\frac{1}{2}}$ is the full peak width in volume units at half of peak height. The calculated plate numbers and standard deviations for the peaks in Graphs 1, 4, 7, and 10 are presented in the following table along with the calculated plate heights.

TABLE I

| Graph. No. | Flow Rate (ml/min.) | $5.54(V_r/W_{\frac{1}{2}})^2$ Plate Number N | $(.425 W_{\frac{1}{2}})$ Standard Deviation (ml) | H (L/N) Plate Height (mm) |
|---|---|---|---|---|
| 1 | 0.5 | 42.5 | 0.74 ml | 6.6 mm |
| 4 | 1.0 | 31.4 | 0.84 | 8.9 |
| 7 | 2.0 | 22.1 | 0.97 | 12.7 |
| 10 | 3.0 | 18.1 | 1.06 | 15.5 |

The following expression is commonly used for plate height dependency on linear velocity or flow rate:

$H = Au0.33 + B/u + Cu$ where H is the plate height, u is the linear velocity (proportional to the volume flow rate) and A, B, and C contants that apply to the particular type of column packing. The B term is due to longitudinal diffusion which is negligible is this situation, and the C term is due to stationary phase mass transfer and doesn't apply to nonporous inert particles. Thus, in this situation, $H = Au0.33 = A'V0.33$ where V is the volume flow rate.

The Golay equation gives peak spreading in an open circular tube as follows:

$$\sigma^2 = \frac{r^4 L \dot{V}}{24 D} = k' \dot{V}$$

where $\sigma^2$ is the variance or standard deviation squared, r is the radius of the tube, L is the length of the tube, $\dot{V}$(dot) is the volume flow rate, and D is the diffusion constant of the liquid.

The number of plates, $n = V_r^2/\sigma^2 = V r^2/k'\dot{V}$

The plate height, $H = L/N = k'\dot{V}$

The plate height for an open circular tube varies proportion to the volume flow rate.

The plate heights based on measured retention volumes and peak widths in Table I are plotted in Graph 15 along with curves for the 0.33 power relationship and the linear relationship expected from the open tube. The dashed curves are normalized to the measured plate height at 1.0 ml/minute. The measured values of H lie between the two dashed curves for the 0.33 power relationship and the linear relationship, but lie closer to the 0.33 power curve expected for an efficiently packed bed. The deviation of measured values from the 0.33 power curve could be explained by channeling a flow along the wall, but this effect could not be too severe or the reduced plate height wouldn't approach a value of 2 at the 0.5 ml/minute flow rate.

Following each of the four injected peak figures are two figures showing gradient profiles generated under the same conditions. One of these two figures is for increasing % B and the other is for decreasing % B. Vertical lines are drawn through the $+\sigma$ and $-\sigma$ distances from the mid level of the gradient profile. A comparison of these figures with Graph II illustrates that the generated gradient profiles closely approximate the error function. Besides providing insight in the process, injected peaks prove useful in sizing the packed bed for a given application. Gradient profiles obtained with different column geometries are shown in Graph 13. Gradient profiles for the 10 ml pipet barrel, the 280 mm long by ¼" diameter Cheminert column, and the double-taper stainless steel column all packed with 3 mm diameter Kimax glass beads are shown. The pipet barrel and the double-taper stainless steel column show shallower gradients with longer approach to equilibrium at the end of the gradient (top of page). Both the shallower gradient and longer approach to equilibrium suggest tailing would be prevalent in these columns. Nevertheless, they would provide useful gradient profiles over most of their range.

The dependence of the gradient profile on length of the packed bed is illustrated in Graph 14 where gradient profiles for 100 mm and 280 mm lengths in the ¼" diameter Cheminert columns are presented. The 280 mm bed gradient reaches 50% B at 2.4 times the time it takes the 100 mm bed gradient to reach the 50% B level, and the time between the 10% and 90% B is about 1.7 times as long for the 280 mm bed gradient. One would expect the ratio of time to reach 50% to be the square root of 2.8 or 1.7 if there were no extra bed contributions to volume and band spreading.

The enclosed graphs produced experimentally, clearly illustrate that the gradient error functions generated by the respective packed bed systems closely approximate those theoretically predicted in Graphs I and II for the exponential dilution chambers connected in series, commonly known to the prior art.

What is claimed is:

1. Apparatus for generating a solvent gradient composition for use in a high performance liquid chromatographic column from a first solvent and a second solvent, the solvent gradient composition approximating an error function, comprising:
   a hollow cylindrical tube having an inlet port and an outlet port, said inlet port permitting the flow of a first solvent and a second solvent into said tube and said outlet port permitting flow of a solvent gradient composition out of said tube;
   a packed bed means located within said tube and between said inlet and outlet ports for generating a solvent gradient composition approximating an error function from said first solvent and said second solvent when said first solvent is passed through said packed bed means and, after the flow of said first solvent through said packed bed means has stopped, said second solvent is subsequently passed through said packed bed means,
   said packed bed means comprising a plurality of chemically inert millimeter sized spherical beads,
   a chromatographic column operatively coupled to said outlet port of said tube, and
   pumping means for sequentially pumping said first solvent into said tube and through said packed bed and chromatographic column and said second solvent into said tube and through said packed bed and, for pumping the solvent gradient composition, as generated by said packed bed means, out of said packed bed means and into said chromatographic column.

2. The apparatus recited in claim 1 wherein each of said beads has a diameter in the range of 3–6 millimeters and said packed bed means has a diameter in the range of ¼–1 inch and a length in the range of 100–280 millimeters.

3. The apparatus recited in claim 1 wherein said pumping means includes means for controlling the flow rate of said second solvent at a predetermined rate.

4. The apparatus recited in claim 3 wherein each of said beads has a diameter in the range of 3–6 millimeters and said packed bed means has a diameter in the range of ¼–1 inch and a length in the range of 100–280 millimeters.

* * * * *